United States Patent [19]
Nigam

[11] Patent Number: 5,928,282
[45] Date of Patent: Jul. 27, 1999

[54] INTRAOCULAR LENS

[75] Inventor: Alok Nigam, Trabuco Canyon, Calif.

[73] Assignee: Bausch & Lomb Surgical, Inc., Claremont, Calif.

[21] Appl. No.: 08/874,753

[22] Filed: Jun. 13, 1997

[51] Int. Cl.$^6$ .................................................. A61F 2/16
[52] U.S. Cl. ............................................................. 623/6
[58] Field of Search ...................................................... 623/6

[56] References Cited

U.S. PATENT DOCUMENTS

| | | | |
|---|---|---|---|
| Re. 32,525 | 10/1987 | Pannu | 623/6 |
| 4,254,509 | 3/1981 | Tennant | 623/6 |
| 4,254,510 | 3/1981 | Tennant | 623/6 |
| 4,316,293 | 2/1982 | Bayers | 623/6 |
| 4,377,873 | 3/1983 | Reichert, Jr. | 623/6 |
| 4,403,353 | 9/1983 | Tennant | 623/6 |
| 4,424,597 | 1/1984 | Schlegel | 623/6 |
| 4,446,581 | 5/1984 | Blake | 623/6 |
| 4,556,998 | 12/1985 | Siepsert | 623/6 |
| 4,605,409 | 8/1986 | Kelman | 623/6 |
| 4,605,411 | 8/1986 | Fedorov et al. | 623/6 |
| 4,629,460 | 12/1986 | Dyer | 623/6 |
| 4,629,462 | 12/1986 | Feaster | 623/6 |
| 4,676,791 | 6/1987 | LeMaster et al. | 623/6 |
| 4,676,792 | 6/1987 | Praeger | 623/6 |
| 4,687,485 | 8/1987 | Lim | 623/6 |
| 4,725,277 | 2/1988 | Bissonette | 623/6 |
| 4,734,095 | 3/1988 | Siepser | 623/6 |
| 4,781,717 | 11/1988 | Grendahl | 623/6 |
| 4,787,904 | 11/1988 | Severin et al. | 623/6 |
| 5,071,432 | 12/1991 | Baikoff | 623/6 |
| 5,078,742 | 1/1992 | Daham | 623/6 |
| 5,133,749 | 7/1992 | Nordan | 623/6 |
| 5,147,395 | 9/1992 | Willis | 623/6 |
| 5,197,981 | 3/1993 | Southard | 623/6 |
| 5,203,790 | 4/1993 | McDonald | 623/6 |
| 5,258,025 | 11/1993 | Fedorov et al. | 623/6 |
| 5,716,403 | 2/1998 | Tran et al. | 623/6 |

FOREIGN PATENT DOCUMENTS

| | | | |
|---|---|---|---|
| 391452B1 | 8/1984 | European Pat. Off. . | |
| WO 87/01931 | 4/1987 | WIPO | 623/6 |

*Primary Examiner*—David J. Isabella
*Attorney, Agent, or Firm*—Pravel. Gambrell, Hewitt, Kimbal & Krieger; Tita D. Vacca

[57] ABSTRACT

A refractive intraocular lens includes an optic portion having an outer peripheral edge and at least two haptic elements each having an inner portion and an outer end for supporting the optic portion in a patient's eye, the respective inner portions of the haptic elements being connected to the outer peripheral edge of the optic portion. Each haptic element includes at least one footplate on the outer end, and further includes a central portion extending between the footplate and the inner portion. The central portion of each haptic element has a greater resistance to bending in a plane generally parallel to an optical axis of the patient's eye than in a plane generally perpendicular to the optical axis. The optical portion and haptic elements are preferably formed of a foldable or compressible material.

19 Claims, 4 Drawing Sheets

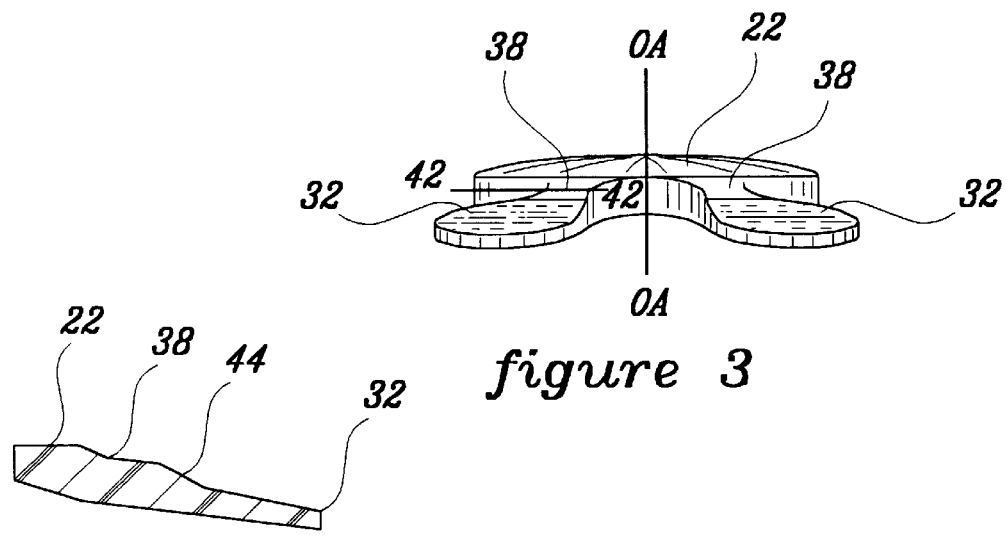
figure 3
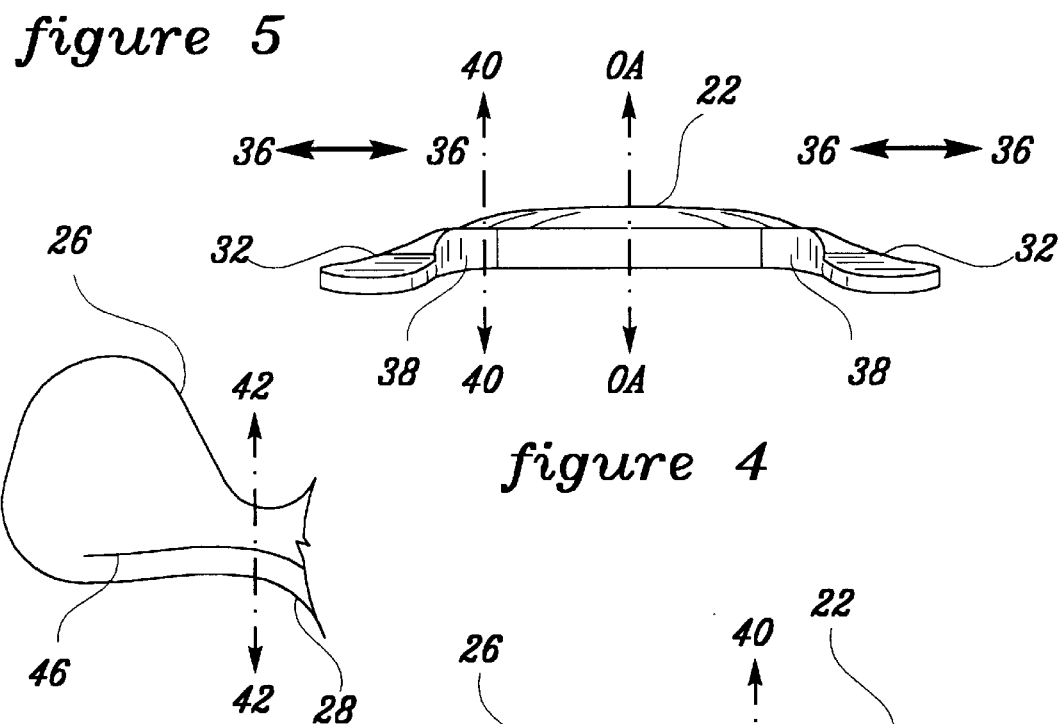
figure 5
figure 4
figure 13
figure 14

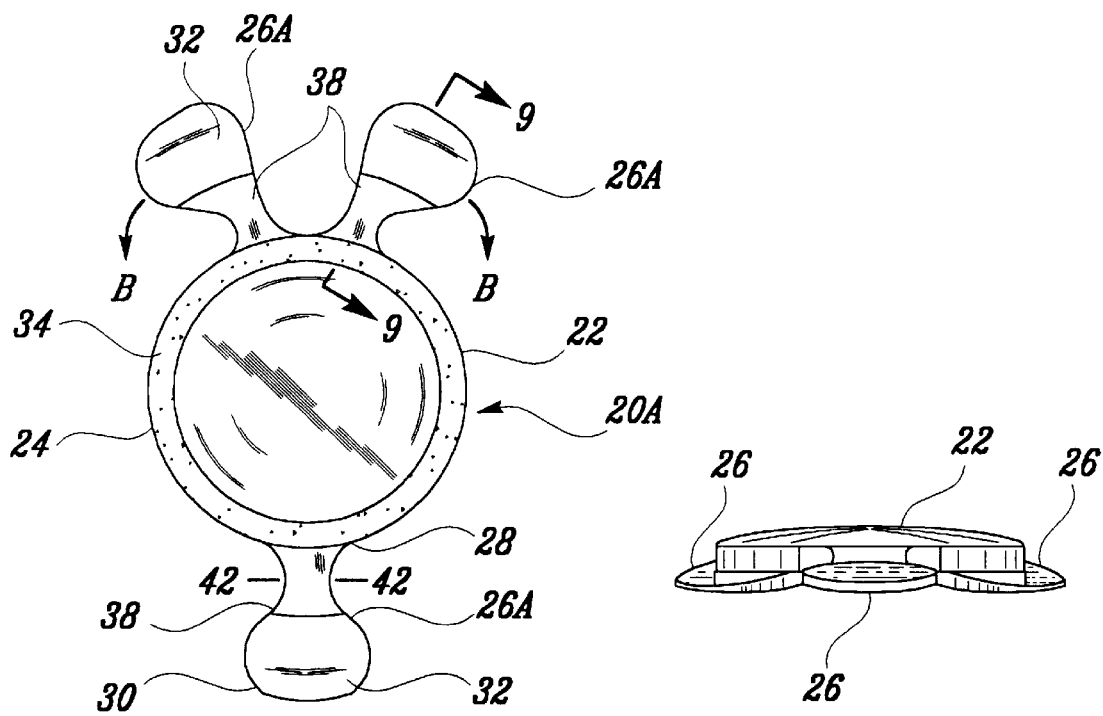
figure 6
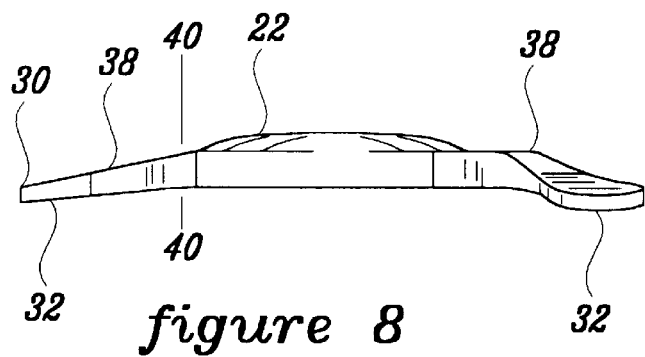
figure 8
figure 7
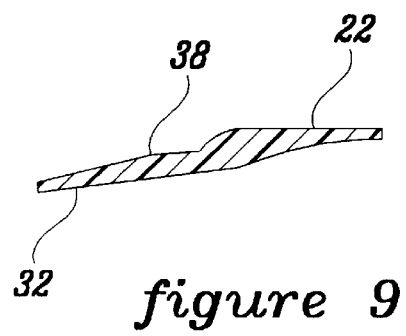
figure 9

INTRAOCULAR LENS

FIELD OF THE INVENTION

This invention relates to intraocular lenses ("IOL"), and more particularly to IOLs designed primarily for refractive correction in phakic eyes where the natural lens remains intact, although IOLs made in accordance with the invention may also be used in aphakic eyes where the natural lens is removed as a result of a cataract.

BACKGROUND OF THE INVENTION

Visual acuity deficiencies such as myopia (nearsightedness) and hyperopia (farsightedness) are typically corrected with use of refractive lenses such as spectacles or contact lenses. Although these types of lenses are effective in correcting a wearer's eyesight, many wearers consider them inconvenient because they have to be located, worn at certain times, removed periodically and can be lost or misplaced. They can also be dangerous or cumbersome if the wearer participates in sports activities or suffers impact to the eye.

The use of IOLs as a permanent form of refractive correction has been gaining popularity. IOLs have been used for years in aphakic eyes as a replacement for the natural crystalline lens of the eye which has been removed as a result of a cataract. Many different designs have been developed and proved to be successful for IOLs used in aphakic eyes. They primarily include an optic portion and supports, called haptics, connected to and surrounding at least part of the optic portion, for supporting the IOL in the eye in either the anterior or posterior chamber.

IOLs have been made from a variety of biocompatible materials, ranging from the so-called rigid materials such as polymethylmethacrylate (PMMA) to the so-called soft materials that can be folded or compressed such as silicones, certain acrylics, and hydrogels. Haptics have been formed separately from the optic portion and connected through processes such as heat or physical staking and chemical bonding. They have also been formed as an integral part of the optic portion in the so-called single piece IOLS.

Soft IOLs have gained popularity because they can be compressed, folded, rolled or otherwise deformed and inserted through an incision in the cornea that is much smaller than necessary for the rigid lenses which must be inserted through an incision slightly larger than the diameter of the optic portion. When implanted in the eye, these soft lenses then open to their original shape because of the memory characteristics of the soft materials.

When implanted, both soft and rigid IOLs are subject to compressive forces exerted on their outer ends, which typically occur when the individual squints or rubs his or her eye. These compressive forces can result in decentration of the optic and distortion of the visual image because the compressive forces tend to cause translational movement along the optical axis. Movement in this direction could cause the IOL to contact and damage the delicate corneal endothelial layer. Also, because IOLs of current designs, whether formed of soft or rigid materials, tend to deflect along the optical axis when the haptics are compressed, IOL manufacturers have had to provide a range of sizes to fit the IOL to a particular patient's eye to minimize the potential for this movement and thus provide more certain refractive correction.

Because of these shortcomings in IOL designs, there is a need for a haptic design that minimizes translational movement of the optic portion along the optical axis when compressive forces are exerted against the outer ends of the haptics.

SUMMARY OF THE INVENTION

An intraocular lens (IOL) made in accordance with the invention has an optic portion with an outer peripheral edge and at least two haptic elements for supporting the optic portion in a patient's eye and is formed of a foldable or compressible material. Each haptic element has an inner portion and an outer end with the inner portion being connected to the outer peripheral edge of the optic portion. Each haptic element includes at least one footplate on the outer end and a central portion that extends between the footplate and the inner portion. The footplates are designed to engage an inner surface of the patient's eye.

The haptic elements have greater resistance to bending in a plane generally parallel to the optical axis of the eye than in a plane generally perpendicular to the optical axis. By providing haptic elements with this type of flexibility characteristic, the inventive IOL can fit eyes of different sizes due to the flexing of the haptic elements relative to the optic portion, without causing unacceptable translational movement of the optic portion along the optical axis when compressive forces are exerted against the haptic elements.

BRIEF DESCRIPTION OF THE DRAWINGS

The invention can be better understood when the detailed description of exemplary embodiments set forth below is considered in conjunction with the appended drawings, in which:

FIG. 3 is a dimensional end view of the IOL of FIG. 2;

FIG. 4 is a dimensional side view of the IOL of FIG. 2;

FIG. 5 is a partial side sectional view of the optic portion, one of the haptic elements and footplate of the IOL of FIG. 2 looking along the site line 5—5 of FIG. 2;

FIG. 6 is a top plan view of an alternate IOL made in accordance with the invention.

FIG. 7 is a dimensional end view of the IOL of FIG. 6;

FIG. 8 is a dimensional side view of the IOL of FIG. 6;

FIG. 9 is a partial side sectional view of the optic portion and one of the haptic elements of the IOL of FIG. 6 looking along the site line 9—9 of FIG. 6;

FIG. 13 is a top plan view of a haptic element and footplate with an embedded stiffening element; and FIG. 14 is a side sectional view of the haptic element and footplate of FIG. 13.

DETAILED DESCRIPTION OF INVENTION

Figure 1:
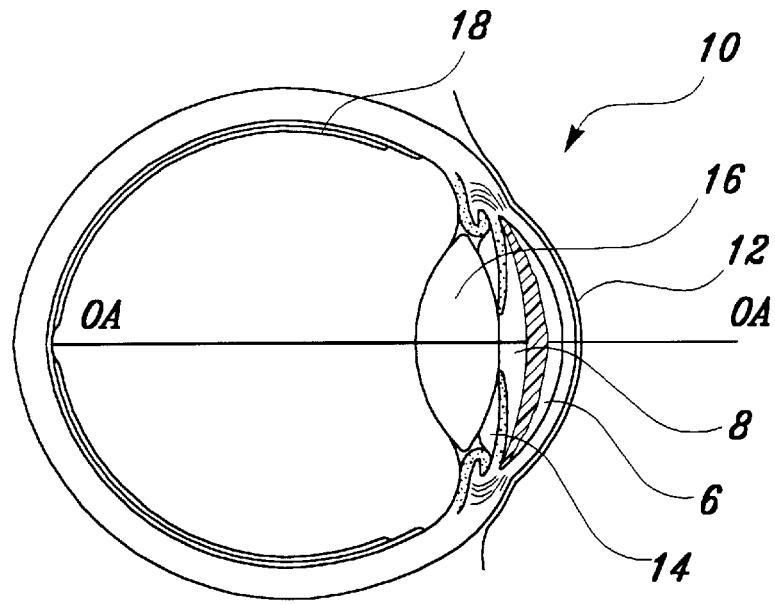
FIG. 1 is a schematic representation of the interior of the human eye, that includes the natural lens and a refractive IOL implanted in the anterior chamber.
Figure 2:
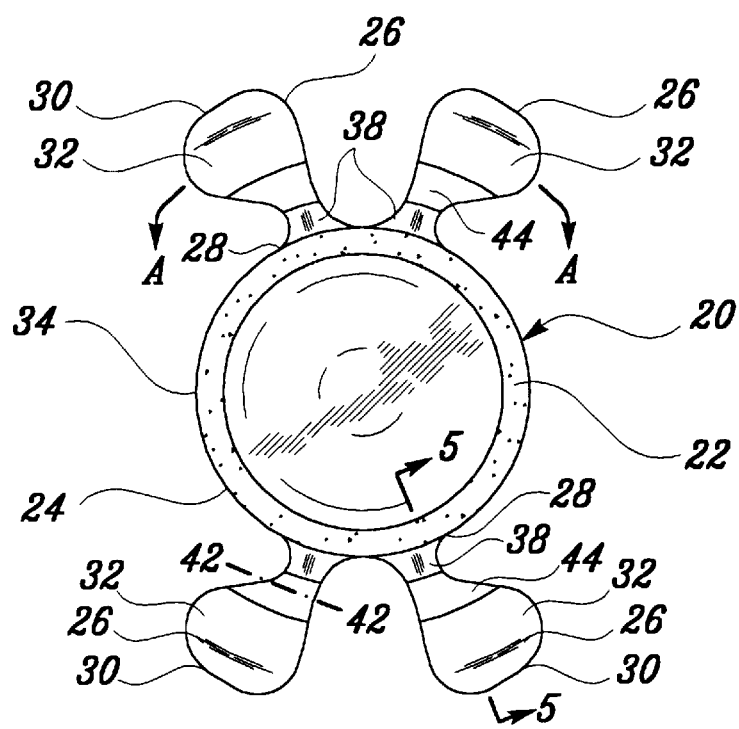
FIG. 2 is a top plan view of an IOL made in accordance with the invention.

FIG. 1 illustrates a simplified diagram of an eye 10 showing landmark structures relevant to the implantation of an intraocular lens of the present invention. The eye 10 includes an optically clear cornea 12 and an iris 14. A natural crystalline lens 16 and a retina 18 are located behind the iris 14. The eye 10 also includes an anterior chamber 6 located in front of the iris 14 and a posterior chamber 8 located between the iris 14 and the natural lens 16. The IOLs of the present invention are preferably implanted in the anterior chamber 6 to correct refractive errors when the natural lens 16 remains in place (phakic application). IOLs of the present invention may also be implanted in the posterior chamber 8, and may be used in aphakic eyes as a replacement for a natural lens 16 in cataract surgery. The eye 10 also includes an optical axis OA—OA which is an imaginary line that passes through the optical centers of both surfaces of any lens, and in the human eye is generally perpendicular to the cornea 12, the natural lens 16 and the retina 18 of the eye 10.

The IOL of the present invention is designed with flexibility characteristics that cause the supports or haptic elements to move toward the optic portion when compressive forces are exerted on their outer ends, with minimal translational movement along the optical axis OA—OA for preventing decentering of the IOL, distortion of vision, and corneal endothelial touch. These flexibility characteristics also permit one or several standard lens sizes of each style to be suitable for eyes of most sizes. By providing universal lenses of this type, the risk of implanting an improper sized lens is reduced, which is beneficial to the patient because many clinical problems, such as pupil ovalization, corneal endothelial damage and poor fixation are eliminated. Also, the need to make IOLs of many sizes for each style is eliminated and inventory costs are reduced. An IOL made in accordance with the subject invention is more forgiving from a size point of view and the ophthalmologist saves time by not having to measure the patient's eye chamber and select a specific size IOL for each procedure.

Although the present invention is preferably applied to soft or foldable IOLs, which are formed of a foldable or compressible material, it can also be used in conjunction with the so-called hard lenses which have optic portions formed of a relatively rigid material such as polymethylmethacrylate (PMMA) and have flexible haptics either formed of the same ("single-piece IOLS") or different ("multiple-piece IOLS") material.

The preferable soft material of the lens of the present invention is a hydrogel known as hefilcon A, which has a high water content and refractive index greater than the aqueous humor of the eye (+1.33), a feature that is desirable to impart optical power for use as a refractive lens. This material also has the mechanical strength to withstand physical manipulation during implantation and good memory properties so that the IOL can unfold in the eye into a predetermined shape and have dimensional stability in the eye. However, other suitable foldable or compressible materials, such as silicone polymers, hydrocarbon and fluorocarbon polymers, other hydrogels, soft acrylic polymers, polyesters, polyamides, polyurethane, silicone polymers with hydrophilic monomer units, fluorine-containing polysiloxane elastomers and combinations thereof could also be used.

When used as a refractive lens, the optic portion can be a positive powered lens from 0 to approximately +20 diopters, or a negative powered lens from 0 to approximately −25 diopters. The optic portion can be biconvex, plano-convex, plano-concave, biconcave or concave-convex (meniscus), depending upon the power required to achieve the appropriate central and peripheral thickness for efficient handling.

One embodiment of the present invention is shown in FIGS. 2–5 where an IOL, identified by reference numeral 20, is designed for implantation preferably in the anterior chamber of a patient's eye. The IOL 20 has an optic portion 22 with an outer peripheral edge 24. In this embodiment, four separate haptic elements 26, each having an inner portion 28 and an outer end 30, are connected through their inner portions 28 to the outer peripheral edge 24 of the optic portion 22. Each haptic element 26 also includes a relatively flat footplate 32, that is designed to engage the inner surface of the eye through the rounded outer end 30. The haptics may be integrally formed with the optic or the haptics may be attached by staking, chemical polymerization or other known methods.

The optic portion 22 can be formed with a glare reduction zone 34 adjacent to the outer peripheral edge 24 for reducing glare where the edge of the lens is struck by light entering the pupil or during high light or at other times when the pupil is dilated. The glare reduction zone 34 is typically fabricated of the same material as the optic portion 22, but may be opaque, colored or patterned to block or diffuse light in the optical plane.

In accordance with the invention, the haptic elements 26 are designed so that when the IOL 20 is implanted in a patient's eye and held in place through compressive forces exerted on the outer ends 30 of the haptic elements 26, the haptic elements 26 will flex in a plane 36—36 (FIG. 4) in the direction of arrows A (FIG. 2), generally perpendicular to an optical axis OA—OA of the IOL 20. By designing this type of flexibility characteristic into the haptic elements 26, an IOL 20 of one or several standard sizes will be suitable for most sizes of patient's eyes because little, if any, translational movement of the IOL 20 will occur in a direction generally parallel to the optical axis OA—OA when compressive forces of different magnitudes (i.e., as caused by eyes of different sizes) are exerted against the outer ends 30 of the haptic elements 26. Another benefit of the IOLs designed in accordance with the present invention is protection of the corneal endothelium from contact by the IOL when compressive forces are applied to the eye because the IOL will not move into contract with the endothelium.

This flexibility characteristic can be achieved in several different ways. In IOL 20 shown in FIGS. 2–5, the haptic elements 26 are formed with a central portion 38 adjacent to the optic portion 22, central portion 38 has a dimension in the plane 40—40 (generally parallel to the optical axis OA—OA (FIG. 4)), that is equal to or greater than a dimension in the plane 42—42 (FIG. 3) (generally perpendicular to the optical axis OA—OA). A transition portion 44, of a decreasing size in the dimension 40—40, extends from the central portion 38 to the footplate 32. The footplates 32 are relatively flat (see FIGS. 3, 4).

Typical dimensions for an IOL of this style include generally: a 5.5 mm diameter optic portion 22 that is about 0.7 mm thick at the peripheral edge 24; haptic portions 26 that are about 3.5 mm long from their inner portion 28 to the outer end 30; a central portion 38 that is about 1.5 mm long, about 0.7 mm thick in the plane 40—40 and about 0.7 mm wide in the plane 42—42; a transitional portion that is about 0.5 mm long; and a footplate 32 that is about 3.0 mm wide, about 2.0 mm long and about 0.3 mm thick.

Thus, the haptic elements 26 gradually change from being relatively thin (in the plane 40—40) at the footplates 32, to being relatively thick at the connection of the inner portion 28 and the optic portion 22, with the central portion 38 in this design being generally equal in the plane 40—40 and in the plane 42—42. Haptic elements with this shape in the direction of arrows A in FIG. 2, will tend to flex toward the optic portion 22 when a compression force is exerted against the outer ends 30, with a minimal translational motion along the optical axis OA—OA. When the IOL 20 is used as a refractive lens, a stable, reliable refractive correction is provided.

Another IOL 20A, made in accordance with the invention, is shown in FIGS. 6–9, where two haptic elements 26A are provided on one side of the optic and one haptic element 26 is provided on the other side. The flexibility characteristic of the IOL 20A is provided for in a different way than that described above for IOL 20. Instead of a transition portion 44, the haptic elements 26 have a greater thickness in the plane 42—42 than in the plane 40—40. As shown in particular in FIGS. 8 and 9, the footplates 32 gradually increase in thickness from the outer ends 30 to the central portion 38, with the central portions 38 having a width that is of a much greater diameter than that in the plane 40—40. This shape allows the haptic elements 26B to flex toward the optic portion, as shown by arrows B in FIG. 6, as a compressive force is exerted against the outer ends 30.

Figure 10:
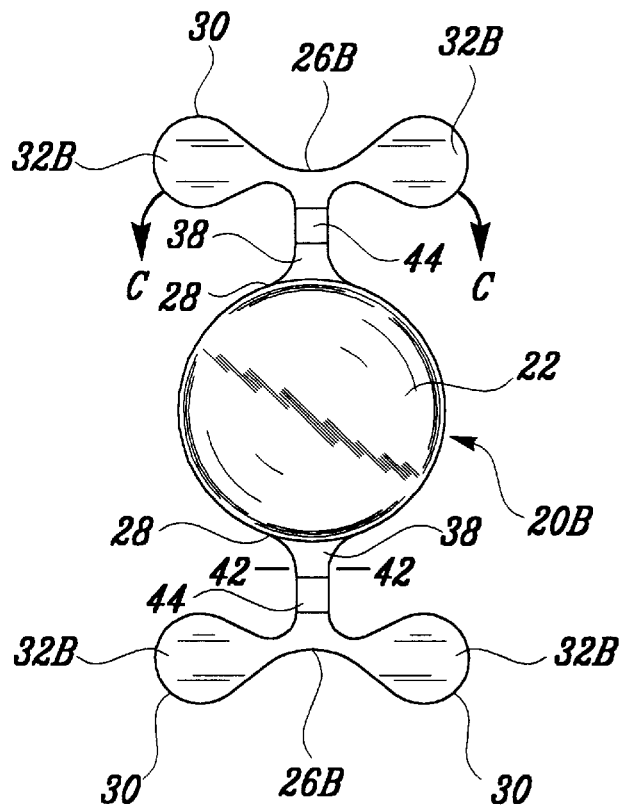
FIG. 10 is a top plan view of an alternate IOL made in accordance with the invention.
Figure 11:
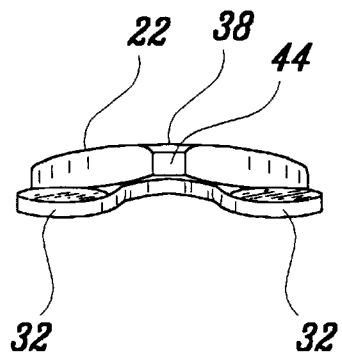
FIG. 11 is a dimensional end view of the IOL of FIG. 10.
Figure 12:
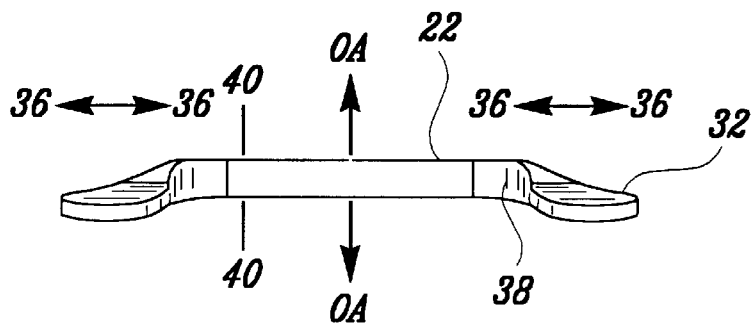
FIG. 12 is dimensional side view of the IOL of FIG. 10.

Another embodiment of the inventive lens, IOL 20B, is shown in FIGS. 10–12. The IOL 20B has two haptic elements 26B with a pair of footplates 32B formed at the outer end of each haptic element 26B. Alternatively, a pair of footplates 32B can be formed on only one haptic element 26B with the opposing side of the optic portion 28 having a haptic element of another suitable design.

IOL 20B also includes an inner portion 28 and an outer end 30. The haptic elements 26B are connected through thin inner portions 28 to the outer peripheral edge 24 of the optic portion 22. The footplates 32B are designed to engage the inner surface of the eye, through the rounded outer end 30.

As in IOL 20, the haptic elements 26B are designed so that when IOL 20B is implanted in a patient's eye and held in place through compressive forces exerted on the outer ends 30 of the haptic elements 26B, the haptic elements 26B will flex in a plane 36—36 (FIG. 12) in the direction of arrows C (FIG. 10) generally perpendicular to an optical axis OA—OA of the IOL 20B.

The flexibility characteristics of the IOL 20B is achieved by the haptic elements 26B being formed with the central portion 38 having a dimension in the plane 40—40 (generally parallel to the optical axis OA—OA (FIG. 12)), that is equal to or greater than a dimension in the plane 42—42 (generally perpendicular to the optical axis) (FIGS. 10 and 12). A transition portion 44, of a decreasing size in the dimension 40—40, extends from the central portion 38 to the junction of the footplates 32B. The footplates 32B are relatively flat (FIGS. 11 and 12). Haptic elements with this shape will tend to flex toward the optic portion 22 when a compressive force is exerted against the outer ends 30, with a minimal translational motion along the optical axis OA—OA.

Another way the desired flexibility characteristic of the IOLs of the present invention can be achieved is by incorporating a stiffening element 46, in the shape of a ribbon, in one or more of the haptic portions 26, as shown in FIGS. 13 and 14. The ribbon 46 is formed of a relatively strong material. It can be used in conjunction with the haptic shapes described above, or it can be used with conventional haptic designs to achieve the desired flexibility characteristics.

The ribbon 46 can be inserted so that its flat face is oriented parallel to the dimension 40—40 as shown in FIG. 14. The ribbon 46 can also be inserted to conform to the curvature of the edges of the haptic element 26, as shown in FIG. 13. The ribbon 46 is formed of a material that is relatively stiff compared to the material of the haptic element. Suitable materials can include a polyimide, polyolefin, HDPE, polyester, nylon, metal or any other material with suitable stiffening characteristics. The material does not have to be biocompatible when it is totally encapsulated in the IOL. The ribbon 46 operates like an I-beam to prevent translational movement along the optical axis OA—OA when compressive force is applied to the outer ends of the haptic elements 26.

The IOLs of the present invention provide for a refractive lens that can be manufactured in a number of different styles that are suitable for use in the anterior chamber of the eye. The inventive IOL has haptics with flexibility characteristics that allow only minimal translational motion along the optical axis OA—OA, therefore preventing decentration of the lens, distortion of vision, and damage to the corneal endothelial cells. The IOLs of the present invention with these flexibility characteristics are also advantageous because only one or several sizes of lens of each style is needed to accommodate the eyes of most patients. By providing universal lenses of this type, the clinical risks to patients because of improper lens size are minimized and the need to make IOLs of many sizes for each style is eliminated and inventory costs are reduced.

Although particular embodiments of the invention have been described in detail for purposes of illustration, various modifications may be made without departing from the spirit and scope of the invention as defined by the appended claims.

What is claimed is:

1. An intraocular lens to be positioned generally perpendicular to an optical axis of an eye when implanted in a patient's eye, comprising:

(a) an optic portion having an outer peripheral edge;
    (b) at least two haptic elements each having an inner portion and an outer end for supporting the optic portion in a patient's eye, the respective inner portions of the haptic elements being connected to the outer peripheral edge of the optic portion;
    (c) each haptic element including at least one footplate on the outer end, and further including a central portion extending between the footplate and the inner portion; and
    (d) substantially the entire central portion of each haptic element having a greater resistance to bending in a plane generally parallel to an optical axis of the patient's eye than in a plane generally perpendicular to the optical axis.

2. The intraocular lens of claim 1, wherein the optic portion and haptic elements are formed of a foldable or compressible material.

3. The intraocular lens of claim 2, wherein the foldable or compressible material is selected from the group consisting of silicone polymers, hydrocarbon and fluorocarbon polymers, hydrogels, soft acrylic polymers, polyester, polyamides, polyurethane, silicone polymers with hydrophilic monomer units, fluorine-containing polysiloxane elastomers and combinations thereof.

4. The intraocular lens of claim 3, wherein the hydrogel material is hefilcon A.

5. The intraocular lens of claim 1, wherein the footplates are relatively flat in a plane generally perpendicular to the optical axis.

6. The intraocular lens of claim 1, wherein the central portion of at least one haptic element is formed with a dimension equal to or greater in a plane generally parallel to the optical axis than in a plane generally perpendicular to the optical axis.

7. The intraocular lens of claim 6, wherein all of the haptic elements have a central portion formed with a dimension equal to or greater in a plane generally parallel to the optical axis than in a plane generally perpendicular to the optical axis.

8. The intraocular lens of claim 1, wherein the central portion of one haptic element is formed with a dimension equal to or greater in a plane generally perpendicular to the optical axis than a dimension of the footplate in a plane generally perpendicular to the optical axis.

9. The intraocular lens of claims 7 or 8, wherein the haptic elements include a transition zone of increasing thickness in a plane generally parallel to the optical axis, the transition zone extending from the footplate to the central portion.

10. The intraocular lens of claim 6, wherein the inner portion of the at least one haptic element has a dimension in a plane generally parallel to the optical axis that is essentially the same as a dimension of the central portion and a dimension of the optic portion in planes generally parallel to the optical axis.

11. The intraocular lens of claim 1, wherein the at least two haptic elements include two haptic elements on a first side of the optic portion and at least one haptic element on a second side of the optic portion.

12. The intraocular lens of claim 1, wherein the at least two haptic elements include two haptic elements on a first side of the optic portion and two haptic elements on a second side of the optic portion.

13. The intraocular lens of claim 1, wherein the at least two haptic elements include one haptic element on a first side of the optic portion and a second haptic element on an opposite side of the optic portion, with two of the at least one footplate connected to the outer end of at least one of the haptic elements.

14. The intraocular lens of claim 1, wherein a glare reduction zone is formed adjacent to the outer peripheral edge of the optical portion.

15. The intraocular lens of claim 1, and further including a stiffening element incorporated in at least one of the haptic elements, the stiffening element having a greater resistance to bending in the plane generally parallel to the optical axis than in the plane generally perpendicular to the optical axis.

16. The intraocular lens of claim 15, wherein the stiffening element is formed of an elongated length of material having a dimension in a plane generally parallel to the optical axis greater than a dimension in a plane generally perpendicular to the optical axis.

17. The intraocular lens of claim 15, wherein the stiffening element extends into the footplate.

18. The intraocular lens of claim 15, wherein the stiffening element is formed of a material selected from the group consisting of polyimide, polyolefin, HDPE, polyester, nylon and metal.

19. The intraocular lens of claim 15, wherein all of the haptic elements include the stiffening element.

* * * * *